United States Patent
Leonard et al.

(10) Patent No.: US 7,794,645 B2
(45) Date of Patent: Sep. 14, 2010

(54) METHOD FOR PRODUCING A BIODEGRADABLE, SYNTHETIC AND FLEXIBLE DIAPHYSEAL OBTURATOR

(75) Inventors: Alain Leonard, Caixon (FR); Cyril Sender, Toulouse (FR)

(73) Assignee: Teknimed S.A., Vic En Bigorre (FR)

( * ) Notice: Subject to any disclaimer, the term of this patent is extended or adjusted under 35 U.S.C. 154(b) by 340 days.

(21) Appl. No.: 11/772,336

(22) Filed: Jul. 2, 2007

(65) Prior Publication Data

US 2009/0008813 A1    Jan. 8, 2009

(51) Int. Cl.
*C08J 5/00* (2006.01)
*B29C 47/76* (2006.01)
*B28B 1/20* (2006.01)
*B28B 1/00* (2006.01)
*B28B 7/34* (2006.01)
*A61F 2/00* (2006.01)

(52) U.S. Cl. .................. 264/331.18; 264/101; 264/313; 425/2; 424/423; 249/61; 623/901

(58) Field of Classification Search ............ 264/331.18, 264/101, 313; 424/423; 425/2; 249/61; 623/901
See application file for complete search history.

(56) References Cited

U.S. PATENT DOCUMENTS 3,709,809 A * 1/1973 Wright et al. ............ 204/192.3

4,093,175 A * 6/1978 Putzer et al. ................ 249/153
2008/0081881 A1* 4/2008 Swetlin et al. ............. 525/424

FOREIGN PATENT DOCUMENTS

FR    2763500    10/2003
WO    03/064496    8/2003
WO    03/089492    10/2003

OTHER PUBLICATIONS

Search Report.
Nagata et al., "Synthesis and enzymatic degradation of regular network aliphatic polyesters", XP-002468752, Reactive & Functional Polymers, vol. 30, 1996, pp. 165-171.

* cited by examiner

*Primary Examiner*—Monica A Huson
*Assistant Examiner*—Michael T Piery
(74) *Attorney, Agent, or Firm*—Mintz, Levin, Cohn, Ferris, Clovsky and Popeo, P.C.; Brian Hopkins; Sheridan Snedden

(57) ABSTRACT

The present invention relates to a method for preparing a biodegradable piece for medical use including the steps of:
a) preparing a mixture including glycerol and sebacic acid,
b) pouring said mixture into a one-piece mould made of elastic material,
c) placing the mould containing said mixture on a support,
d) placing the support into a chamber with controlled temperature and vacuum level until a polymer having the desired consistency is obtained,
e) removing the support from the chamber and allowing it to cool down to room temperature, and
f) removing the piece thus obtained from the mould.

16 Claims, 2 Drawing Sheets

Figure 1:
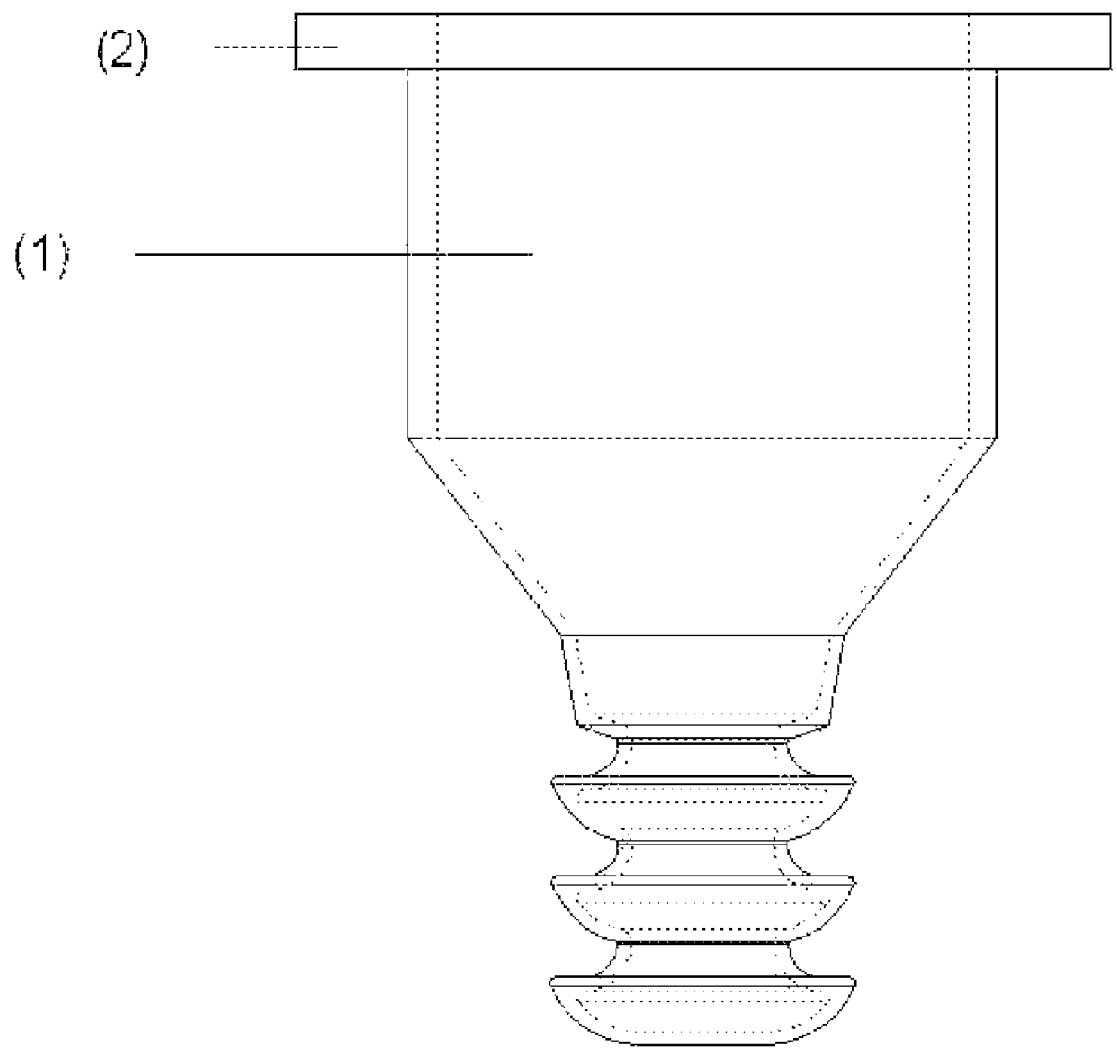

METHOD FOR PRODUCING A BIODEGRADABLE, SYNTHETIC AND FLEXIBLE DIAPHYSEAL OBTURATOR

This invention relates to the field of medical devices used in bone surgery, and in particular to systems for closing the medullary canal used in the sealing of a prosthesis. It relates to a method for preparing a biodegradable item for medical use, such as a diaphyseal obturator, in which poly(glycerol sebacate) is formed in entirely smooth elastic surface moulds.

Total prostheses (hip, knee, etc.) make it possible to replace a damaged joint and thus to relieve the pain and improve the patient's mobility. The main indications for implantation of this type of implant are joint degeneration and certain fractures.

In total cemented hip arthroplasty, a prosthesis is inserted into the medullary canal and attached to it with an acrylic cement, generally based on PMMA (polymethyl methacrylate). The polymerization reaction of the monomer is produced in a few minutes. The implantation of a total cemented hip prosthesis requires good preparation of the bone surfaces and homogeneous and total filling of the proximal canal with the acrylic cement. The insertion of the prosthesis into the medullary canal filled with cement causes a pressurization of the latter, which has a tendency to move away from the implanted zone through the proximal orifice or by coming into contact with the bone marrow. These vacuums are responsible for stress concentration and breaking point phenomena. To avoid these phenomena, the use of a diaphyseal obturator introduced into the medullary canal at the base of the implanted zone is necessary. The primary function of the obturator is to prevent the formation of these vacuum zones of cement around the prosthesis by limiting the progression of cement into the distal portion. It makes it possible not only to avoid the diffusion of the PMMA and its monomer into the bone marrow but also to increase the intramedullary pressure on impaction of the prosthesis and therefore to promote good stability of the prosthesis by interpenetration of the cement into the surrounding bone tissues.

The benefit of occlusion of the femoral stem in total cemented hip arthroplasty is fully established today. The obturator must be sterile, biocompatible and sufficiently flexible to adapt to the irregularities in shape of the diaphyseal canal. The obturator has been produced with various types of plugs described in the prior art:
- acrylic cement plug,
- polyethylene (PE), silicone, polyethylene terephthalate (PET), or polyetheretherketone (PEEK) plug,
- spongy bone plug, taken from the osteotomy part or from the upper portion of the medullary canal,
- plug made of bioresorbable material based on gelatine, polylactic acid or PEGT/PBT copolymer (Polyactive™).

Depending on the type, these obturators have drawbacks. Some are too rigid and do not make it possible to sufficiently engage with the shape of the femoral canal so as to prevent cement leakages. This high rigidity also causes these systems to have a tendency toward distal migration on impaction of the prosthesis. They are primarily non-biodegradable, which complicates the surgical intervention in a possible subsequent operation. Indeed, this extraction must be performed without generating debris responsible for the well-known osteolysis phenomenon, and increases the duration of the intervention.

The bioresorbable polylactic acid obturators can cause inflammatory responses in some patients, and the use of spongy bone is proscribed because the formation of a bone bridge that is difficult to remove is frequently observed.

Gelatine-based plugs do not have such drawbacks and are currently widely used. Nevertheless, as they are constituted primarily of gelatine of porcine origin, they can be considered to be potential vehicles of pathological entities (prions, etc.) and for some patients have an allergenic character. The health safety requirements now require the use of medical devices that are free of any uncertainty about their innocuousness, in accordance with the precautionary principle. Finally, their use on Jewish or Muslim patients may be inappropriate. The limitation or prohibition of this type of product must be precluded by the development of a new plug.

The plug obtained according to the method of the invention affords the physicochemical and mechanical properties necessary for its function, it is totally free of any substance capable of causing a risk to the health of the patients. The method according to this invention thus makes it possible to obtain a polymer replacing the porcine gelatine-based formulation currently used. After carrying out preliminary laboratory tests on various systems, it was discovered that the polymer called PGS for poly(glycerol sebacate) satisfied all of the criteria of the specifications defined above, on the condition that it is produced under well-defined conditions making it possible to obtain solid compact and homogeneous pieces, free of any structural defects. This new material is entirely synthetic, bioresorbable and has elastic properties similar to the current product.

The PGS thus produced is obtained by direct polycondensation of glycerol and sebacic acid. It is known and used in the field of tissue engineering as a culture medium. However, its use is limited in the form of thin ribbed films for guiding the formation of tissues. It is also used in the form of a wire, particles, tube, fibre or woven screens. Only pieces of very low thickness are obtained by the polymerization method described heretofore in the prior art (WO 03/064496). This method consists of condensing a mixture of glycerol and sebacic acid at 120° C. according to a two-step pressure cycle in rigid polytetrafluoroethylene (PTFE) moulds in which a water-soluble mould release agent is recommended. However, for solid pieces on the order of the centimeter and with complex shapes, moulds composed of a plurality of parts must conventionally be used. Nevertheless, when the mixture reaches freezing point and while it is still viscous and without mechanical strength, the presence of bubbles promoted by the temperature and pressure conditions at the level of the mould line(s) at the junction of the various parts of the mould deform the moulded piece, resulting in a heterogeneous mass with volume and surface defects, which weaken the piece and reduce its mechanical strength properties. The term "freezing point" designates the time at which the mean molar mass of the polymer and its viscosity suddenly increase toward infinity.

It has therefore not been possible heretofore to produce biocompatible, bioresorbable and totally synthetic diaphyseal obturators that are solid and homogeneous, free of structural defects, and of which the mechanical properties are similar to those of current gelatine-based products. This invention solves these problems with a method for producing a PGS-based polymer, of which the procedure conditions make it possible to obtain a solid piece with a complex, compact and homogeneous shape. It has in particular been demonstrated that it is crucial to prevent the formation of bubbles in the casting of the monomer mixture into the moulds and that the choice of the moulds was of major importance.

The term compact refers to the character of a solid, massive three-dimensional structural piece, by comparison with a porous or lacunary structure, or in the form of a film or a wire.

The homogeneity means that the compact character is uniform throughout the entire mass of the piece in question. These two characteristics result in a structure free of internal or surface structural defects, without a zone of reduced strength or reduced elasticity capable of causing breakage by tearing.

More specifically, this invention relates to a method for preparing a biodegradable piece for medical use including the steps of:

a) preparing a mixture including glycerol and sebacic acid, without using any solvent, b) pouring said mixture into a one-piece mould (regardless of the dimensional complexity of the piece to be moulded), made of elastic material, c) placing the mould containing said mixture on a support made of a thermally conductive material, d) placing the support holding the mould containing said mixture into a vacuum chamber with heating plates at a temperature in the range of 80° C. to 150° C., under a pressure in the range of 5 mbar to 500 mbar, until a polymer having a consistency suitable for its function is obtained (similar to that of the gelatine-based CEMSTOP® diaphyseal obturator), e) removing the support from the chamber and allowing it to cool down to room temperature, and f) removing the piece thus obtained from the mould, by opening (optionally tearing) and pulling off the elastic wall of the mould in contact with the moulded piece.

The direct polycondensation of glycerol and sebacic acid, i.e. respectively of a triol and a linear carboxylic diacid, results in the formation of a thermosetting copolymer. At room temperature, the sebacic acid is a powder form (its melting point is 130° C.). The glycerol is a viscous liquid. The two monomers can be mixed by bringing the sebacic acid to a liquid state and by mixing it with glycerol. This procedure has the advantage of being solvent-free, as solvent traces could lead to the release of harmful or toxic substances into the body after implantation of the obturator. The molar ratio of glycerol/sebacic acid is less than 1. According to a preferred feature of the invention, the mixture of glycerol and sebacic acid is obtained by liquefaction of the latter in the first at 150° C. This step can be performed in an inert atmosphere in order to avoid any oxidation of the monomers and to prevent yellowing of the mixture.

An advantage of this invention lies in the fact that the entire method can be performed solvent-free throughout.

Steps a), d) and e) of the method according to this invention can preferably be carried out in an inert atmosphere.

The liquid monomer mixture is poured into a mould (in practice, in industrial conditions, into a series of moulds) that has the special feature of being made of a one-piece elastic material. The essential advantage with respect to conventional rigid moulds made of two or more shells is that it is free of any parting plane that, no matter how fine it is, creates a discontinuity in the junction of the two shells. This discontinuity has been found to be the cause of the formation of bubbles not enabling a compact and homogeneous piece to be obtained during polymerization under reduced pressure. The visible parting plane on the moulded piece constitutes a zone of reduced strength causing the piece to weaken under strong mechanical stresses. The use of a perfectly smooth internal surface mould without a parting plane solves this problem. The elasticity of the moulds makes it possible to develop pieces with a complex shape and facilitates their removal from the mould without damage. For this type of application, it must also be of a medical or food use grade.

Figure 2:
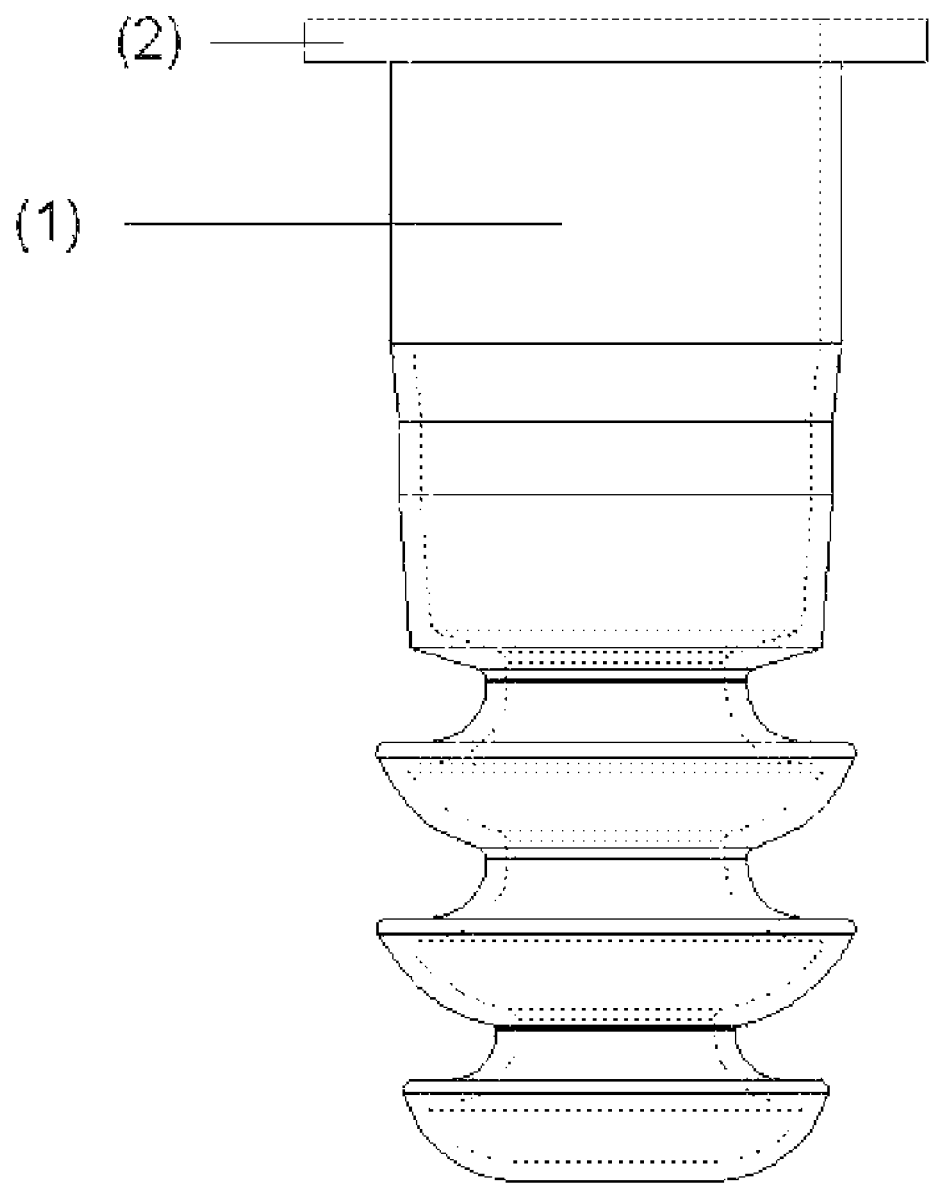

FIGS. 1 and 2 show two silicone moulds making it possible to obtain obturators with a diameter of 8 and 18 millimeters according to the method of this invention.

According to a preferred feature of the invention, the mould includes a container 1 with an upper edge 2 capable of supporting said mould resting on its support. The thickness of the wall is chosen according to the tear strength of the material that constitutes the mould.

According to an advantageous feature of the method of this invention, the mould inserted into its support slightly larger (several millimeters at most) than the longest external diameter of the cast makes it possible to obtain polymerized pieces in a very homogeneous manner. A uniform degree of polymerization is noted over the entire height of the pieces, which is not the case when aluminum or polytetrafluoroethylene casts are used. This phenomenon is attributed to the low spacing between the mould and its support, promoting radial heat exchanges, and therefore a homogeneous distribution of the heat transmitted to the reaction mixture.

The mould used in the method of this invention preferably has its largest cross-section at the level of the upper opening of the container 1. The mould support is made of a thermally conductive material and with an internal shape intimately engaging the general external profile of the moulds.

According to a preferred feature, the polymerization of the PGS is performed under reduced air pressure or an inert gas, so as to progressively remove the water produced by the polymerization reaction. This makes it possible to accelerate the reaction kinetics and to reduce the time and costs of production. The pressure level is below 500 mbar.

The polymerization temperature must be high enough for the sebacic acid not to harden in the monomer mixture, but not be so high as to cause the formation of bubbles in the volume of the mixture. The minimum and maximum temperatures of the method according to the invention have been determined as 80° C. and 150° C., respectively. According to the invention, the working temperature can be chosen according to the kinetics of the polymerization reaction, which is faster at high temperature.

When the polymerization has reached the point at which it gives the moulded piece the desired consistency, the reaction is stopped by cooling back to room temperature. The product obtained is stable, so that it is possible to immediately remove it from the mould or store it as is. The mould removal must be performed without damaging the piece obtained. The elasticity of the mould and its low tear strength is used to advantage in order to remove it gently. A person skilled in the art knows how to assess this parameter by several simple tests on the chosen material. The polymerized piece, then elastic, can be hardened by a preliminary cooling between −15° C. and −25° C. in a freezer in order to facilitate this step.

The method described above can be implemented to produce any solid PGS piece, in particular biodegradable items for medical use. It is particularly suitable for use in the production of a diaphyseal obturator.

EXAMPLE

The example below is intended to show an embodiment of this invention without limiting the scope thereof.

Synthesis of a Solid and Compact PGS Piece

1. Preparation of the Monomer Mixture

Glycerol and sebacic acid are added to a melter heated to 150° C. and swept across the surface with a gaseous nitrogen stream so as to prevent the oxidation of the monomers in contact with the air. Stirring is provided by a propeller at low speed in order to prevent bubbles from forming in the mixture. The mixture is kept under stirring until complete dissolution of the acid in the glycerol.

2. Casting of the Mixture

The monomer mixture is cast at 150° C. into the moulds placed on their support through the opening of a bottom valve of the melter tank. The volume of mixture is measured according to the size of the piece to be produced. The elasticity of the moulds allows for easy deformation and manual removal of any air bubbles that may have been trapped in the irregularities of the cast. The moulds are made of food- or medical-grade silicone, in one piece, and have no discontinuity or roughness at the internal surface associated with their production.

3. Polymerization

The moulds filled and positioned on their support are arranged in a vacuum chamber with heating plates. This device makes it possible to simultaneously control the temperature, the vacuum level of the chamber and the maintenance of an inert atmosphere preventing yellowing of the PGS. The temperature is fixed at 130° C. and the pressure at 200 mbar. The inert atmosphere is obtained by successive venting of the chamber with 2 to 3 emptying/filling cycles using a vacuum pump and a neutral gas tank connected to the chamber. The water produced by the monomer polycondensation reaction is evacuated by evaporation at the interface of the reaction medium with the surrounding gas. The polymerization time ranges between 2 and 3 days for a PGS volume of 1 mL.

The product obtained is an elastomer having elastic properties comparable to those of the porcine gelatine currently used to produce diaphyseal obturators (CEMSTOP® type). The moulded pieces have no surface defects or gaseous inclusion capable of adversely affecting their quality, in particular with regard to the tear strength.

The invention claimed is:

1. Method for preparing a biodegradable piece for medical use including the steps of:
   a) preparing a mixture including glycerol and sebacic acid,
   b) pouring said mixture into a one-piece mould made of elastic material,
   c) placing the mould containing said mixture on a support, wherein the mould support is made of a thermally conductive material with an internal shape intimately engaging the general external profile of the moulds wherein said internal shape is slightly larger than the longest external diameter of the mould,
   d) placing the support into a chamber with controlled temperature and vacuum level until a polymer having the desired consistency is obtained,
   e) removing the support from the chamber and allowing it to cool down to room temperature, and
   f) removing the piece thus obtained from the mould.

2. Method according to the preceding claim, wherein the molar ratio of glycerol/sebacic acid is less than 1.

3. Method according to claim 1 wherein the method is carried out solvent-free throughout.

4. Method according to claim 1, wherein steps a), d) and e) are performed under an inert atmosphere.

5. Method according to claim 1, wherein step d) is performed at a temperature in the range of 80° C. to 150° C.

6. Method according to claim 1 wherein step d) is performed at a pressure in the range of 5 to 500 mbar.

7. Method according to claim 1, wherein the mould removal of the piece is performed by opening and pulling off the elastic wall of the mould in contact with the moulded piece.

8. Method according to claim 1, wherein, prior to the separation of the mould from the moulded piece, the mould and the piece that it contains are cooled down to a temperature in the range of −15° C. to −25° C.

9. Method according to claim 1, wherein the mould includes an upper edge (2) for supporting said mould resting on the support.

10. Method according to claim 1, wherein the inner dimension of the mould has its highest cross-section at the level of the upper opening of the container (1).

11. Method according to claim 1, wherein the elastic material comprises silicone.

12. Method according to claim 1, wherein the elastic material is silicone.

13. Method according to claim 1, wherein mixture consist essentially of glycerol and sebacic acid.

14. Method according to claim 1, wherein consists of glycerol and sebacic acid.

15. Method according to claim 13, wherein the molar ratio of glycerol/sebacic acid is less than 1.

16. Method according to claim 15, wherein the molar ratio of glycerol/sebacic acid is less than 1.

* * * * *